(12) United States Patent
Kumar et al.

(10) Patent No.: US 11,484,519 B2
(45) Date of Patent: Nov. 1, 2022

(54) D-SERINE INHIBIT NEUROINFLAMMATION DUE TO A BRAIN INJURY

(71) Applicant: Florida State University Research Foundation, Inc., Tallahassee, FL (US)

(72) Inventors: Sanjay S. Kumar, Tallahassee, FL (US); Stephen Beesley, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 183 days.

(21) Appl. No.: 16/812,677

(22) Filed: Mar. 9, 2020

(65) Prior Publication Data

US 2020/0289449 A1   Sep. 17, 2020

Related U.S. Application Data

(60) Provisional application No. 62/815,150, filed on Mar. 7, 2019.

(51) Int. Cl.
*A61K 31/198* (2006.01)
*A61P 25/28* (2006.01)
*A61K 9/00* (2006.01)

(52) U.S. Cl.
CPC .......... *A61K 31/198* (2013.01); *A61K 9/0019* (2013.01); *A61K 9/0073* (2013.01); *A61P 25/28* (2018.01)

(58) Field of Classification Search
CPC .................................................. A61K 31/198
See application file for complete search history.

(56) References Cited

U.S. PATENT DOCUMENTS

| | | |
|---|---|---|
| 6,310,097 B1 | 10/2001 | Mitoma et al. |
| 8,404,721 B2 | 3/2013 | Donello et al. |
| 8,492,418 B2 | 7/2013 | Woods |
| 9,040,581 B1 | 5/2015 | Kumar |
| 10,307,387 B1 | 6/2019 | Kumar |
| 2012/0302621 A1 | 11/2012 | Foster et al. |

FOREIGN PATENT DOCUMENTS

| | | |
|---|---|---|
| EP | 1444979 B1 | 12/2009 |
| WO | 2013170072 A2 | 11/2013 |

OTHER PUBLICATIONS

Zaltsman's CAS: 614042548, 2016.*
Chatterton et al., Excitatory Glycine Receptors Containing the NR3 Family of NMDA Receptor Subunits, Nature, vol. 415, Feb. 14, 2002, pp. 793-798.
Kvist et al., Structure-Based Discovery of Antagonists for GluN3-Containing N-Methyl-D Aspartate Receptors, Neuropharmacology, Aug. 24, 2013, pp. 1-13.
Palygin et al., Distinct Pharmacological and Functional Properties of NMDA Receptors in Mouse Cortical Astrocytes, British Journal of Pharmacology, (2011) 163, pp. 1755-1766.
Pilli et al., Triheteromeric N-Methyl-D Aspartate Receptors Differentiate Synaptic Inputs Onto Pyramidal Neurons In Somatosensory Cortex: Involvment of the Glun3A Subunit, Neuroscience 22, (2012), pp. 75-88.
Rauner, Triheteromeric NR1/NR2A/NR2B Receptors Constitute the Major NMDA Receptor Population in Adult Hippocampal Synapses.
Schuler et al.; "Formation of NR1/NRs and NR1/NR3 Heterodimers Constitues the Initial Step in N-Methyl-D-aspartate Receptor Assembly", Journal of Biological Chemistry, vol. 283, No. 1, pp. 37-46, Jan. 4, 2008.
Singh et al., Modulation of Seizure Susceptibility in the Mouse by the Strychnine-Insensitive Glycine Recognition Site of the NMDA Receptor/on Channel Complex, Br. J. Pharmacol. (1990), 99 pp. 285-288.
Wise, Jr. et al., "Hyperaminoaciduria In Rats Following D-Serine Administration", Experimental Biology and Medicine, vol. 121, No. 3, pp. 982-986; 1966.

* cited by examiner

*Primary Examiner* — Rei Tsang Shiao
(74) *Attorney, Agent, or Firm* — Christopher M. Ramsey; GrayRobinson, P.A.

(57) ABSTRACT

D-serine is effective for inhibiting neuron loss due to an immune response by glial cells to a brain injury. An example of a method includes artificially administering a composition including D-serine to brain cells after an injury thereto, the composition including an amount of D-serine effective to inhibit death of neurons.

26 Claims, 8 Drawing Sheets
(8 of 8 Drawing Sheet(s) Filed in Color)

Note morphometric changes in astrocytes (green cells stained with GFAP). Neurons are stained with NeuN (blue). Scale bar = 20 um

D-SERINE INHIBIT NEUROINFLAMMATION DUE TO A BRAIN INJURY

CROSS-REFERENCE TO RELATED APPLICATION

This claims the benefit of priority from provisional Application No. 62/815,150, filed Mar. 7, 2019, the entire contents of which are which are incorporated by reference.

STATEMENT REGARDING FEDERALLY SPONSORED RESEARCH AND DEVELOPMENT

This invention was made with government support under Contract Number R01NS097802 awarded by the National Institutes of Health. The government has certain rights in the invention.

FIELD

This disclosure relates to the field of treating brain injuries and, more particularly, to inhibiting neuroinflammation due to a brain injury.

BACKGROUND

The amino acid D-serine is an agonist of N-methyl-D-aspartate receptors ("NMDARs") in the brain, which are receptor complexes composed of glycine-binding and glutamate-binding subunits. It was reported in U.S. Pat. No. 9,040,581 that D-serine is also an antagonist of GluN3-containing triheteromeric NMDARs, a species of NMDARs found in the temporal lobe and that targeting GluN3-containing triheteromeric NMDARs may be used to treat neurological disorders, such as epilepsy, that cause seizures.

BRIEF SUMMARY

It has now been discovered unexpectedly that D-serine inhibits neuroinflammation of brain cells after a brain injury by reducing the neurotoxic immune response of glial cells after the injury. Accordingly, D-serine may be used in the treatment of brain injuries to help prevent neural cell loss caused by harmful immune responses.

In a first example, a method of inhibiting neuron loss after an injury to brain cells comprises artificially administering a composition comprising D-serine to brain cells after an injury thereto. The composition includes an amount of D-serine effective to inhibit death of neurons due to an immune response to the injury by glial cells. Additional optional features of this method may include one or more of the following features.

The artificially administering step may be performed within 170 hours from when the injury occurred.

The injury may be a traumatic brain injury.

The injury may be a concussion.

The injury may be a non-traumatic brain injury selected from stroke, tumor, hypoxia, infection, and/or encephalitis.

The composition may be a solution having a D-serine concentration of 1 µM to 500 µM.

The artificially administering step may be achieved by inhalation of the composition.

The artificially administering step may be achieved by injecting a temporal lobe of a patient's brain with the composition.

When the artificially administering step is performed, a patient to whom the composition is artificially administered has not been diagnosed with temporal lobe epilepsy.

In a second example, a method comprises treating a patient having developed a brain injury and inhibiting the brain injury from precipitating into temporal lobe epilepsy by artificially administering a composition comprising D-serine to the patient. The composition includes an amount of D-serine effective to inhibit death of neurons due to an immune response by glial cells of an injured portion of the patient's brain. Additional optional features of this method may include one or more of the following features.

The artificially administering step may be performed within 170 hours from the when the patient received the brain injury.

The brain injury may be a traumatic brain injury.

The brain injury may be from a blow to a head of a patient to whom the composition is artificially administered.

The brain injury may be a concussion.

The brain injury may be a non-traumatic brain injury selected from stroke, tumor, hypoxia, infection, and/or encephalitis.

The composition may be a solution having a D-serine concentration of 1 µM to 500 µM.

Artificially administering may be achieved by inhalation of the composition.

Artificially administering may be achieved by injecting a temporal lobe of the patient's brain with the composition.

When the artificially administering step is performed, the patient has not been diagnosed with temporal lobe epilepsy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF EXAMPLE EMBODIMENTS

Figure 1:
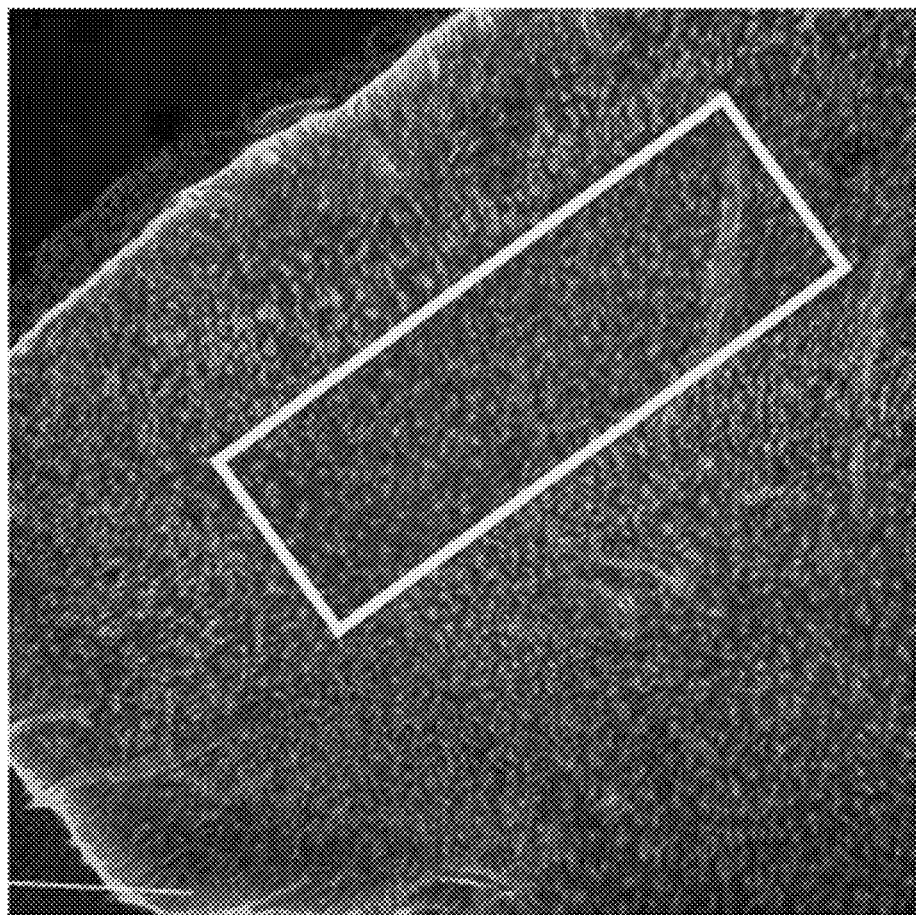
FIG. 1 is a brain slice image from a control experiment where the tissue shows no precipitating brain injury.

Brain cells called glial cells provide support and protection for neurons. Types of glial cells include oligodendrocytes, astrocytes, ependymal cells, Schwann cells, microglia, and satellite cells. Astrocytes and microglia are of particular importance to the role of D-serine in preventing neuro inflammation.

Astrocytes, which are the most abundant cell-type in the brain, have many different functions, including maintaining osmotic balance, maintaining ionic conditions for neurons, neurotransmitter recycling, and metabolite homeostasis. See Sajjja et al, *Frontiers in Integrative Neuroscience,* Vol. 10, Art 7, pgs. 1-9 (February 2016). This makes astrocytes indirectly involved in most brain functions. Id.

Microglia are the immune cells of the central nervous system, which arrive at the injury site to initiate an inflammatory immune response that is supposed to prevent further cell damage due to an injury. Id.

Subsequent to a brain injury, astrocytes and microglia secrete cytokines to the injured area, which causes inflammation to the local tissue, which can kill healthy neurons. Neuronal cell death can the patient to experience neurodegenerative effects.

Because D-serine is naturally produced by the body, the brain may contain a small amount endogenous D-serine at a given time. A normal amount of endogenous D-serine is produced via the body's normal functions. To distinguish endogenous D-serine from the methods described herein, the D-serine in the methods is artificially administered. Endogenous D-serine produced by the body behaving normally is not artificially administered, as described below, because there is no artificial source of, or artificial stimulus for producing, D-serine. In the methods described here, D-serine is artificially administered to a treatment subject such as brain cells and/or a patient.

As used herein, the term "D-serine" includes D-serine, derivatives thereof, and/or pharmaceutically acceptable salt (s) of D-serine and/or its derivatives.

As used herein, the term "treat," means medically treating and includes, by way of example, preventing the onset of, alleviating the severity of, and/or preventing the recurrence of, a particular pathology or symptom of the pathology.

Because D-serine inhibits neuroinflammation of brain cells after a brain injury by reducing the neurotoxic immune response of glial cells after the injury, D-serine has therapeutic efficacy in treating certain brain injuries, particularly, brain injuries that can precipitate into the patient having temporal lobe epilepsy, for example.

In a first method example, D-serine is used to inhibit neuron loss after an injury to brain cells. This method comprises artificially administering a composition comprising D-serine to brain cells after an injury thereto. The composition includes an amount of D-serine effective to inhibit death of neurons due to an immune response to the injury by glial cells.

In a second method example, D-serine is used to treat a brain injury. This method comprises artificially administering a composition comprising D-serine to a patient having a brain injury in an amount effective to inhibit neuron death at the site of the brain injury.

In a third method example, D-serine is used to treat an acute brain injury. This method comprises treating a patient having developed a brain injury and inhibiting the brain injury from precipitating into temporal lobe epilepsy by artificially administering a composition comprising D-serine to the patient. The amount of D-serine is effective to inhibit death of neurons due to an immune response by glial cells of an injured portion of the patient's brain.

In these methods, the injury may be a traumatic brain injury. Examples of traumatic brain injuries include injuries to the brain caused by a traumatic event such as a blow to the head. Traumatic brain injuries include concussions and the like.

In these methods, the injury may otherwise be a non-traumatic brain injury such as a stroke, tumor, hypoxia, infection, and/or encephalitis, among other possible examples.

Certain brain injuries are known to precipitate into temporal lobe epilepsy after the injury occurs. In the methods, D-serine may be used to inhibit the development of temporal lobe epilepsy. In such cases, D-serine may be administered as a prophylactic treatment for neuroinflammation and/or temporal lone epilepsy.

In certain situations, it may be advantageous to artificially administer the D-serine to the patient within 170 hours, 145 hours, 125 hours, 100 hours, 72 hours, 48 hours, or 24 hours from the when the patient received the brain injury. Early administration of D-serine after the patient received the brain injury inhibits the immune response of glial cells at the site of the injury and helps prevent cell death. Treating brain injuries with D-serine soon after their onset may inhibit or prevent the patient from developing temporal lobe epilepsy. By inhibiting temporal lobe epilepsy, D-serine may prevent it from developing or, if it develops, cause the patient to have a less severe case than if D-serine had not been administered.

The time the patient received the brain injury may be measured from the time an acute brain injury occurs. If the injury is due to a traumatic injury such as a blow to the head, then the starting point for measuring when the injury occurred to when D-serine is administered is when the traumatic injury occurred plus or minus four hours.

If the injury is due to a non-traumatic injury such as a stroke, for example, the time the patient received the brain injury may be measured from the time the non-traumatic event that caused the injury commenced plus or minus four hours.

Medical professionals may determine the age of an injury using their medical expertise. They may also use conventional medical measurement techniques such as imaging, blood testing, physical inspection, cognitive testing, and the like.

The temporal lobe is an area of the brain that is particularly vulnerable to brain injuries. Thus, in some examples of the methods, the composition is artificially administered to the patient's temporal lobe. One example of this is when D-serine is artificially administered by injecting a temporal lobe of the patient's brain with the composition.

In particular examples, the composition may artificially administered to a medial entorhinal cortex of the patient's temporal lobe. One example of this is when D-serine is artificially administered by injecting a medial entorhinal cortex of the patient's temporal lobe with the composition.

In these methods, the amount effective to perform its intended function is the minimum amount that provides the intended therapeutic effect on the subject treated. In humans, an effective amount range is often 0.1-1,000 mg/day, including 0.1-25 mg/day, 25-50 mg/day, 50-75 mg/day, 75-100 mg/day, 100-150 mg/day, 150-200 mg/day, 200-250 mg/day, 250-300 mg/day, 300-350 mg/day, 350-400 mg/day, 400-450 mg/day, 450-500 mg/day, 500-550 mg/day, 550-600 mg/day, 600-650 mg/day, 650-700 mg/day, 700-750 mg/day, 750-800 mg/day, 800-850 mg/day, 850-900 mg/day, 900-950 mg/day, 950-1,000 mg/day. Higher doses (1,000-3,000 mg/day) might also be effective.

In a solution dosage form, examples of particular effective amounts of D-serine include, but are not limited to, 1 micromole to 500 micromole, 25 micromole to 175 micromole, 50 micromole to 150 micromole, 75 micromole to 125 micromole, or about 100 micromole.

Examples of possible concentrations off effective amounts of D-serine in a D-serine composition include, but are not limited to, 1 $\mu M$ to 500 $\mu M$, 25 $\mu M$ to 175 $\mu M$, 50 $\mu M$ to 150 $\mu M$, 75 $\mu M$ to 125 $\mu M$, or about 100 $\mu M$.

The effective amount may vary depending on numerous factors, including age, weight, height, severity of the disorder, administration technique, and others. The actual amount of D-serine to be administered in a given case may be determined by a physician taking into account the relevant circumstances.

In these methods, there are many different ways that D-serine may be artificially administered to the brain cells and/or a patient. Artificial administration techniques include, but are not limited to administering one or more pharmaceutically acceptable dosage forms such as suspensions, tablets, suppositories, capsules, injectables, inhalables, transdermals or the like. Other suitable artificial administration techniques include oral, sublingual, buccal, intravenous, subcutaneous, transcutaneous, intramuscular, intracutaneous, intrathecal, epidural, intraocular, intracranial, inhalation, intranasal, or the like. Yet another example of an artificial administration technique is artificially stimulating the production of D-serine within the body. Any combination of these administration techniques may also be used.

D-serine may be an active ingredient in a pharmaceutical composition. In such a case, D-serine may be blended with one or more ingredients useful for making the composition into a pharmaceutically acceptable dosage form such as a suspension, tablet, capsule, injectable, inhalable, or other dosage form that comports with the artificial administration technique. Examples of these ingredients include one or more excipients, diluents, disintegrants, emulsifiers, solvents, processing aids, buffering agents, colorants, flavorings, solvents, coating agents, binders, carriers, glidants, lubricants, granulating agents, gelling agents, polishing agents, suspending agent, sweetening agent, anti-adherents, preservatives, emulsifiers, antioxidants, plasticizers, surfactants, viscosity agents, enteric agents, wetting agents, thickening agents, stabilizing agents, solubilizing agents, bioadhesives, film forming agents, emollients, dissolution enhancers, dispersing agents, or combinations thereof.

In some instances of these methods, it may be advantageous to selectively contact brain cells from the injured area of the brain. Because D-serine is an agonist of conventional NMDARs, one might sometimes want to avoid activating conventional NMDARs in another area of the brain or, at least, minimize D-serine's contact with areas of the brain that are not injured.

Selective contact of brain cells from the injured area of the brain may be achieved by supplying D-serine locally such that the concentration of D-serine within that particular area of the brain is higher than the concentration of D-serine outside that particular area of the brain.

The temporal lobe, including the medial entorhinal cortex, is an area of the brain in which D-serine may be particularly effective for treating injury. For treating an injury to this area of the brain, it might be desirable to artificially administer D-serine by selectively contacting the patient's temporal lobe or, more particularly, the patient's medial entorhinal cortex with D-serine. A preferred selective contact technique for targeting specific areas of the brain involves injecting D-serine into or onto the targeted part of the brain. This can be accomplished by implanting the patient with a D-serine administration device such as a pump or by manual injection through a cannula positioned at the target area of the brain.

EXAMPLE

D-Serine Inhibits Astrocyte Proliferation at the Injury Site and Infiltration of Microglia to the Injury Site This example shows that when D-serine is artificially administered to an injury site where injured brain cells are located, D-serine inhibits the number of, and reactive status of, astrocytes in the region and inhibits infiltration of microglia to the injury site. This example is provided for experimental support and does not limit the scope of what is claimed.

Figure 2:
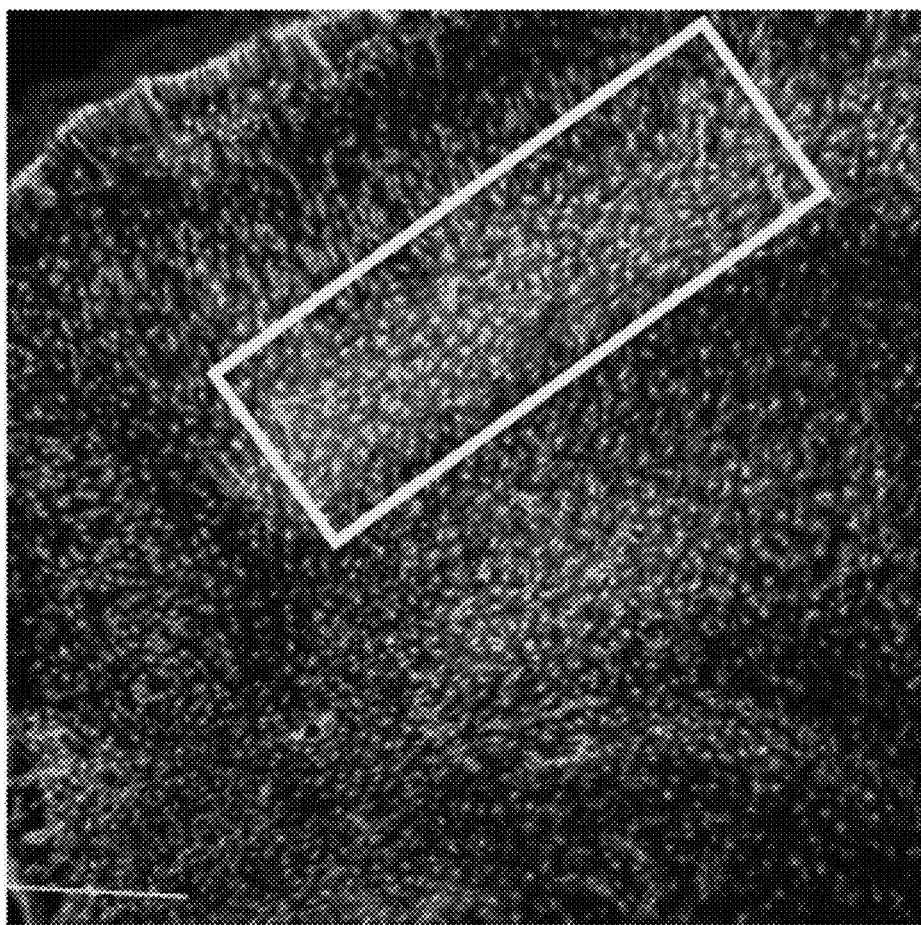
FIG. 2 a brain slice image from an animal perfused with aCSF (vehicle). Note the preponderance of astrocytes (green cells stained with GFAP) and loss of neurons (red cells stained with NeuN) in layer 3 of the MEA (boxed area). DNA is stained with DAPI (blue).
Figure 3:
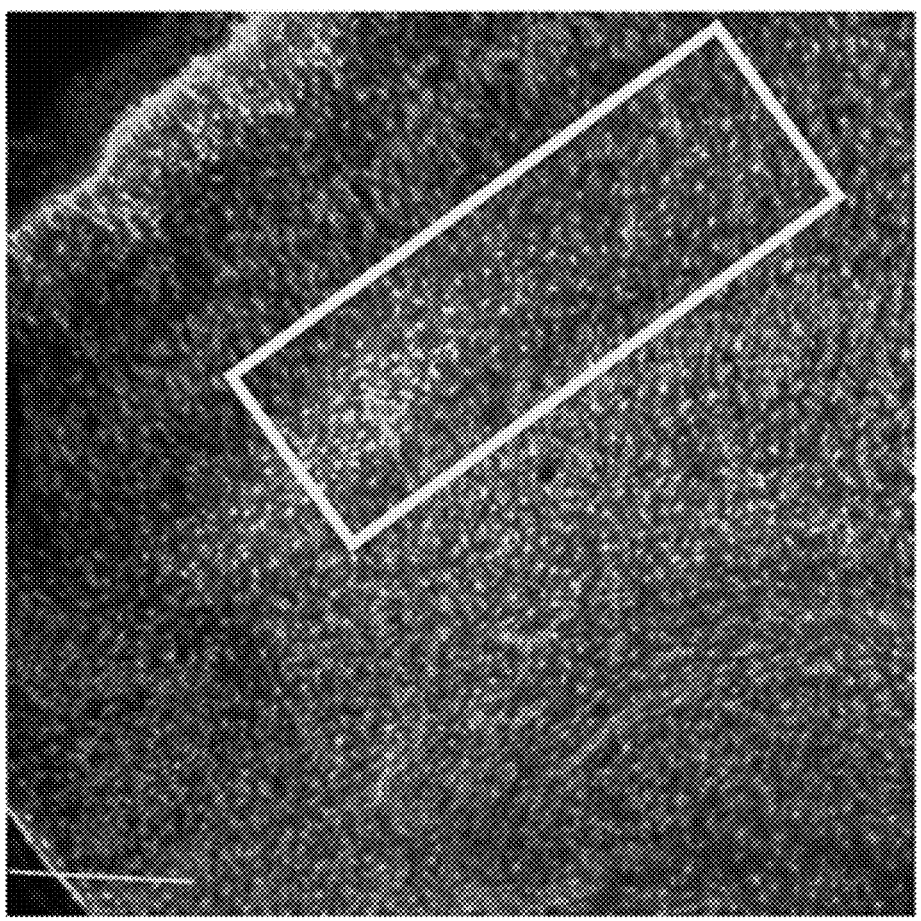
FIG. 3 is a brain slice image from an animal treated with D-serine. Note the difference in astrocytic proliferation (green cells stained with GFAP) and rescue of neuronal cell loss (red cells stained with NeuN) in layer 3 of the MEA.
Figure 4:
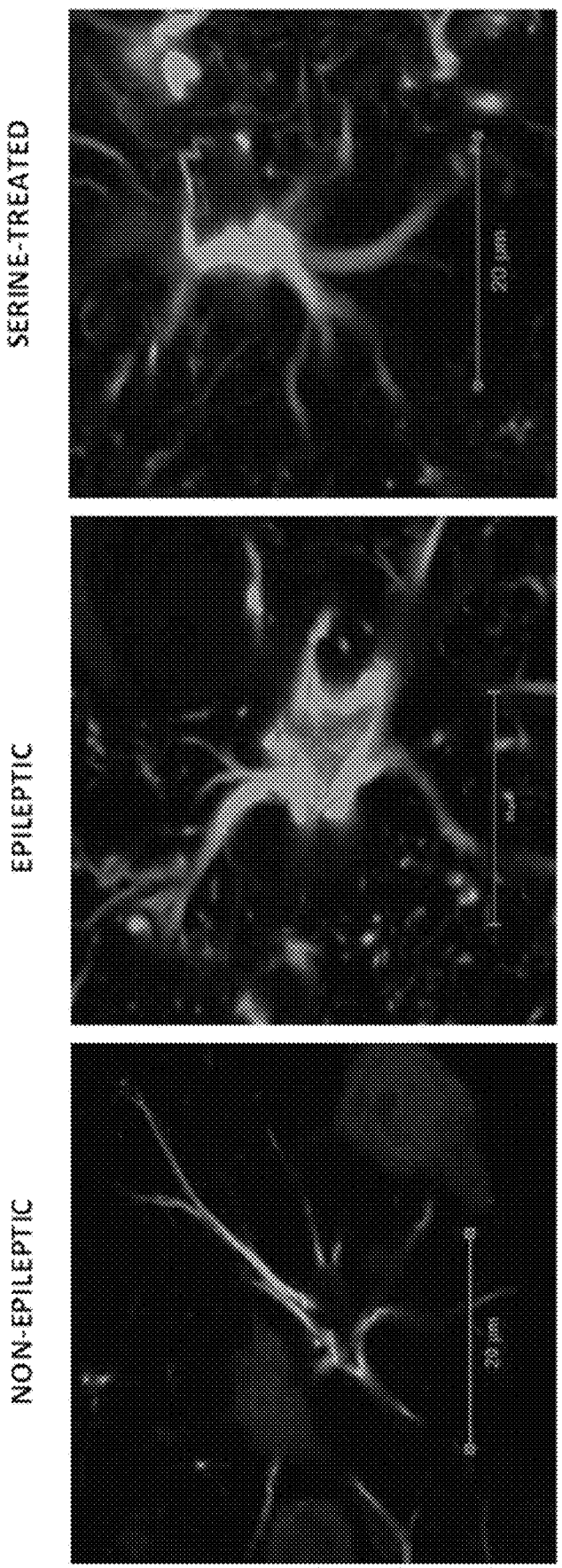
FIG. 4 is a series of images showing morphometric changes in astrocytes in non-epileptic (no brain injury), epileptic (brain injury), and D-serine-treated conditions (green cells stained with GFAP). Neurons are stained with NeuN (blue).
Figure 5:
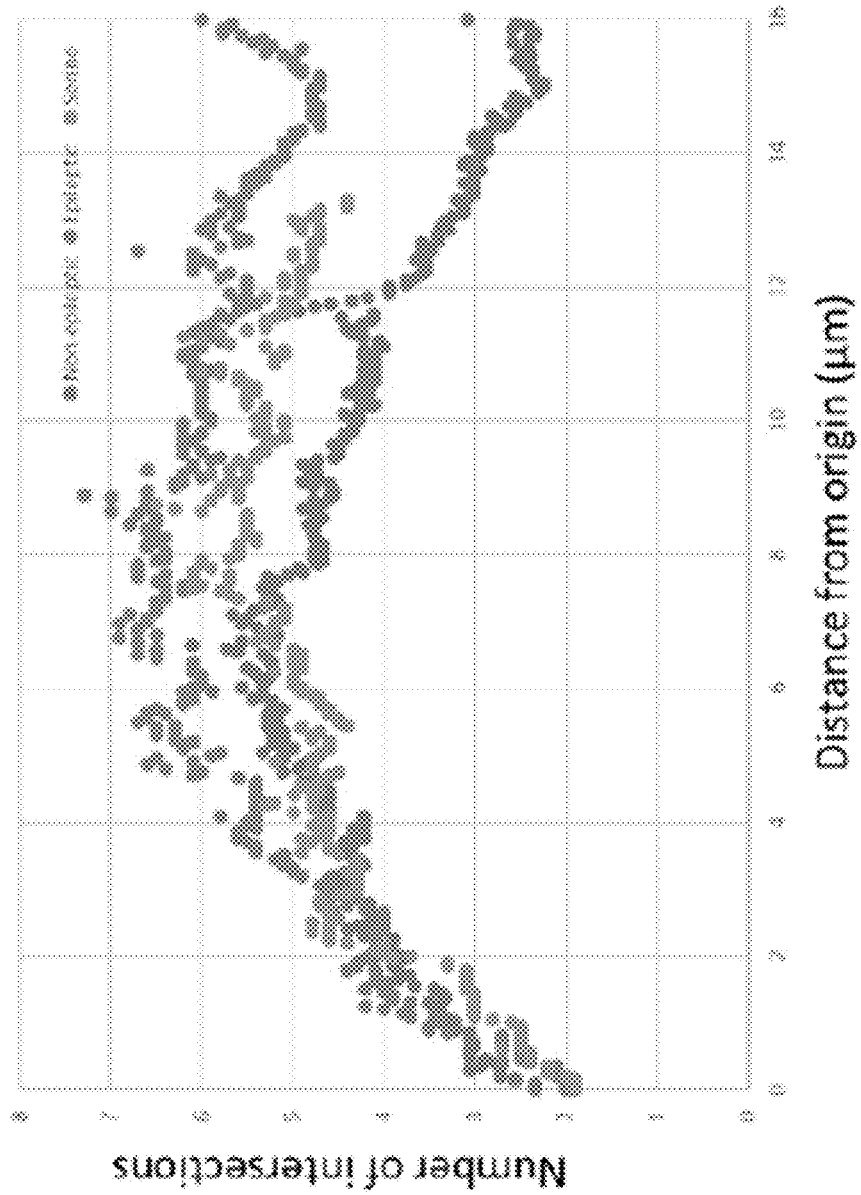
FIG. 5 is a graph of the Scholl analysis of astrocytes in non-epileptic (no brain injury), epileptic (brain injury), and D-serine-treated conditions. Non-epileptic, blue; epileptic, orange; D-serine, grey.
Figure 6:
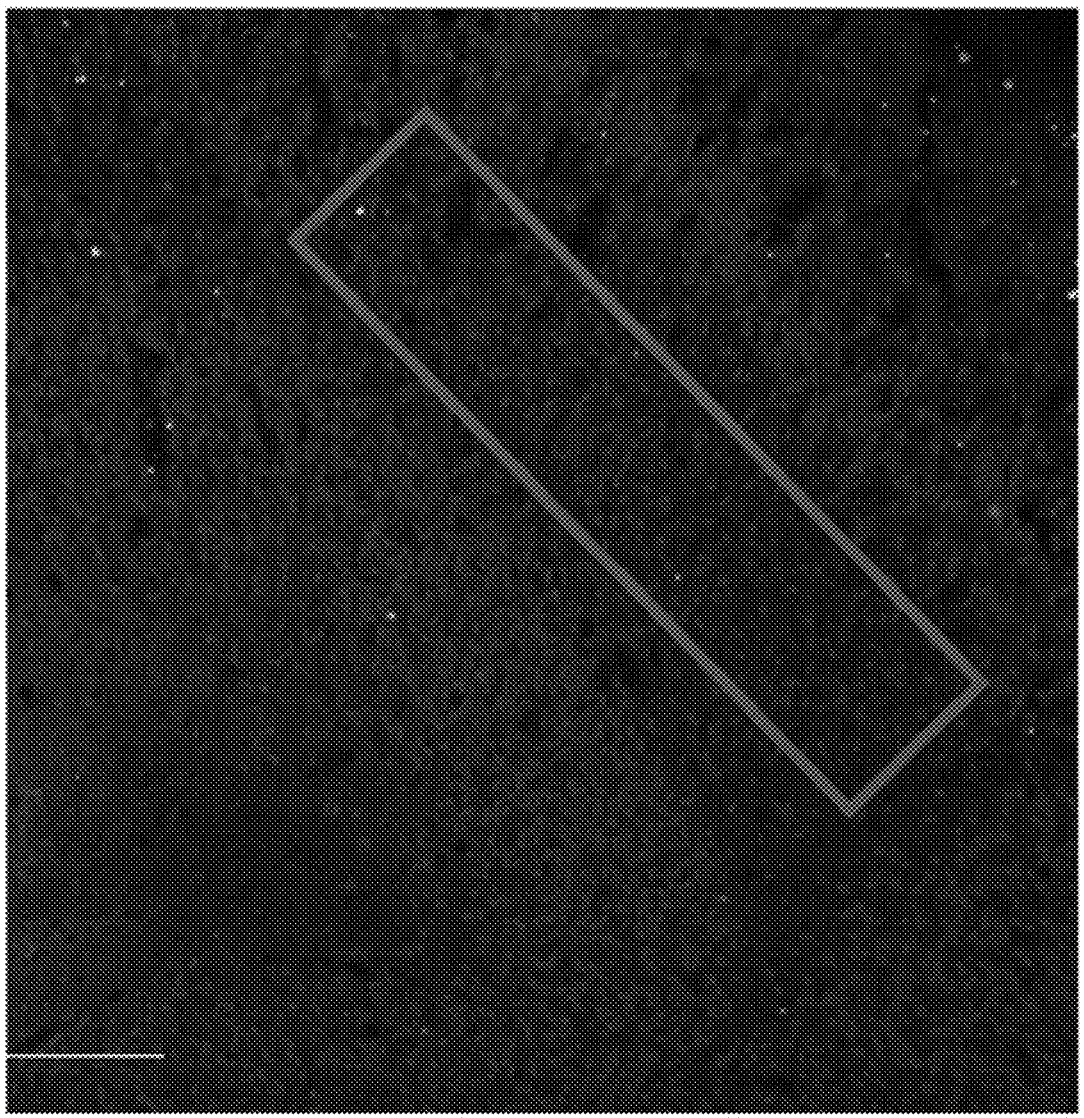
FIG. 6 is a brain slice image from a control experiment where the tissue shows no precipitating brain injury.
Figure 7:
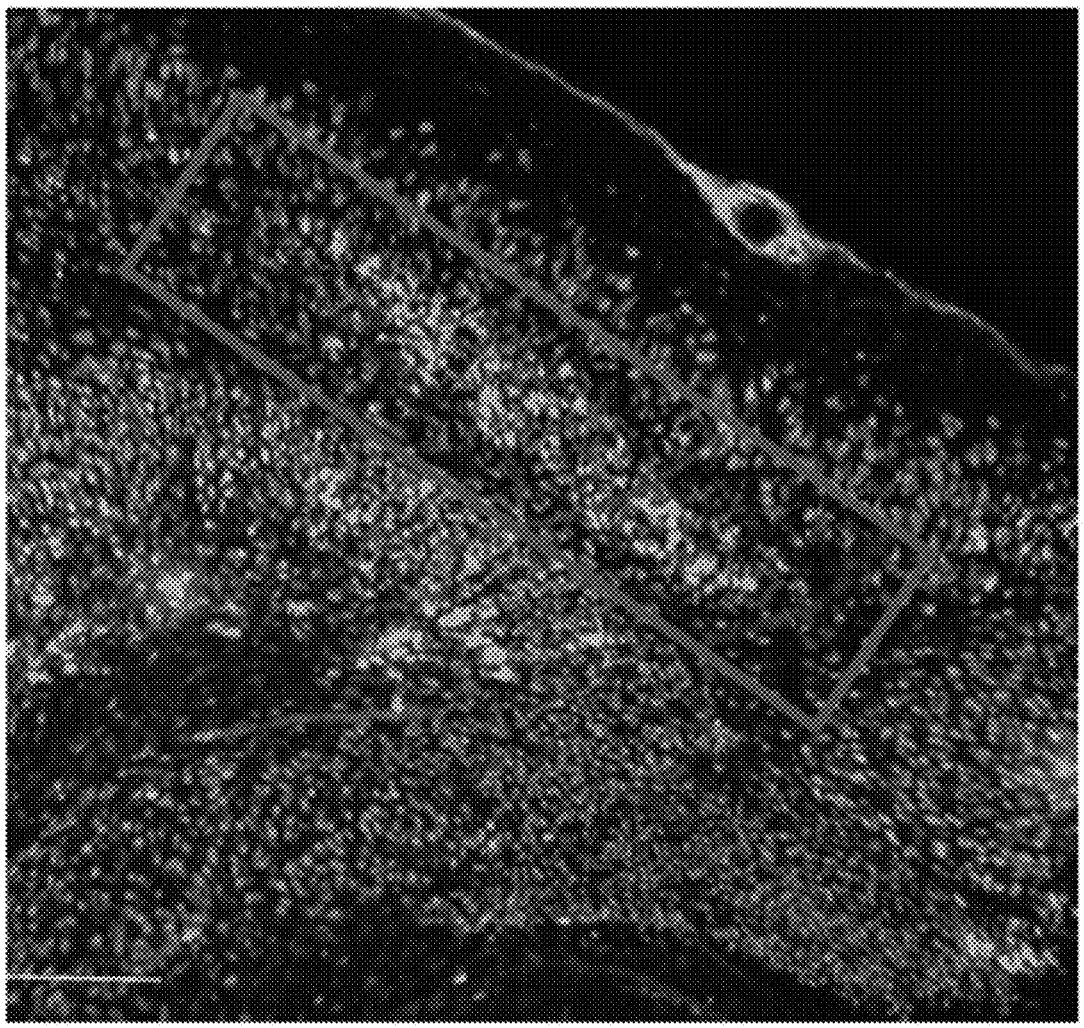
FIG. 7 is a brain slice image from an animal perfused with aCSF (vehicle) that has had a precipitating injury (status epilepticus) and confirmed epileptic through recorded seizure activity. Note infiltration of microglia (green cells stained with OX42) and loss of neurons (blue cells stained with NeuN)
Figure 8:
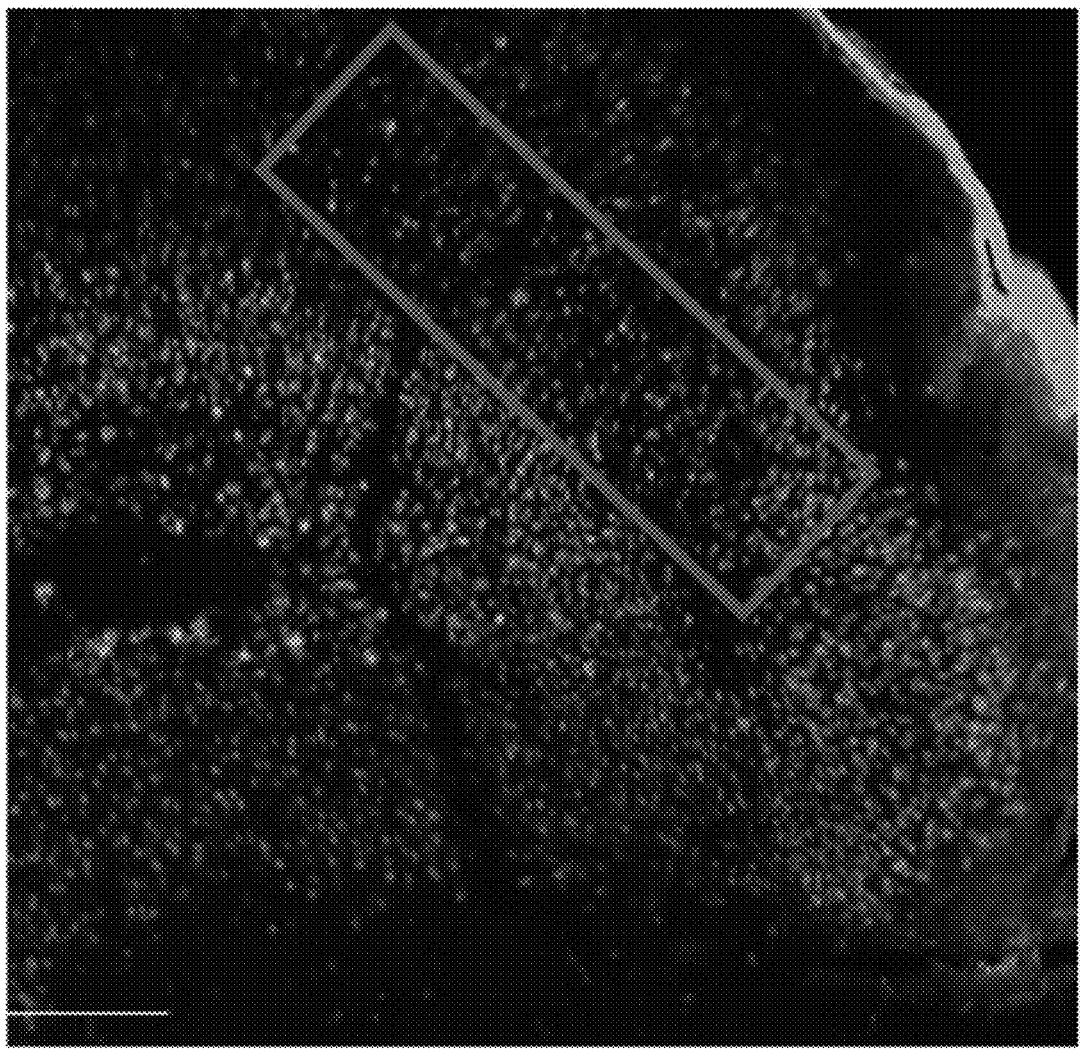
FIG. 8 is a brain slice image from an animal perfused with D-serine that has had a precipitating injury (status epilepticus) but no seizures.

To demonstrate how D-serine prevents neuroinflammation, and neuroinflammation-mediated neuron loss, the numbers and reactive status of astrocytes were assayed (green cells in FIGS. 1-3) and the presence or absence of microglia (green cells in FIGS. 6-8). These cells cause inflammation in brain tissue by releasing cytokines.

These neuroinflammatory cell types were identified using fluorescent-tagged antibodies first in control animals and then in animals that were made epileptic using a well-established animal model of Temporal Lobe Epilepsy. Epileptic animals exhibited significant neuronal loss in the entorhinal area that was accompanied by a pronounced upregulation astrocytes and infiltration of microglia to the region where the cell loss occurred.

In a separate sample of animals, D-serine was injected into the entorhinal area prior to making them epileptic with a chemo-convulsant and immediately after administration of the chemo-convulsant. These animals did not become epileptic. Examination of the entorhinal cortex in these animals revealed a significant rescue of neurons compared with the epileptic animals (red cells, compare FIG. 2 with FIG. 3). In addition, there fewer astrocytes in this region (compare FIG. 2 with FIG. 3) and the infiltration of microglia to this region was significantly reduced (compared FIG. 7 with FIG. 8).

These experiments demonstrate that D-serine not only prevents neuronal loss, it mitigates the deleterious effects of neuroinflammation that contributes to the neuron loss. Because animals administered with D-serine were unresponsive to the epilepsy causing effects of the chemo convulsant and by extension neuron loss and neuroinflammation, D-serine can be used prophylactically to inhibit or prevent seizures and the neuroinflammation from an injury that can precipitate into temporal lobe epilepsy.

This disclosure describes exemplary embodiments, but not all possible embodiments of the compositions and methods. Where a particular feature is disclosed in the context of a particular example, that feature can also be used, to the extent possible, in combination with and/or in the context of other examples. The compositions and methods may be embodied in many different forms and should not be construed as limited to only the examples described here.

The compositions and methods are not limited to the details described in connection with the example embodiments. There are numerous variations and modification of the compositions and methods that may be made without departing from the scope of what is claimed.

That which is claimed is:

1. A method of inhibiting neuron loss after an injury to brain cells, the method comprising artificially administering a composition comprising D-serine to brain cells after an injury thereto, the composition including an amount of D-serine effective to inhibit death of neurons due to an immune response to the injury by glial cells, wherein artificially administering is achieved by inhalation of the composition.

2. The method of claim 1, wherein the artificially administering step is performed within 170 hours from when the injury occurred.

3. The method of claim 1, wherein the injury is a traumatic brain injury.

4. The method of claim 1, wherein the injury is a concussion.

5. The method of claim 1, wherein the injury is a non-traumatic brain injury selected from stroke, tumor, hypoxia, infection, and/or encephalitis.

6. The method of claim 1, wherein the composition is a solution having a D-serine concentration of 1 µM to 500 µM.

7. The method of claim 1, wherein artificially administering is achieved by injecting a temporal lobe of a patient's brain with the composition.

8. The method of claim 1, wherein a patient to whom the composition is artificially administered has not been diagnosed with temporal lobe epilepsy when the artificially administering step is performed.

9. A method comprising,
treating a patient having developed a brain injury; and
inhibiting the brain injury from precipitating into temporal lobe epilepsy by artificially administering a composition comprising D-serine to the patient, including an amount of D-serine effective to inhibit death of neurons due to an immune response by glial cells of an injured portion of the patient's brain, wherein the artificially administering step is performed within 170 hours from when the patient received the brain injury.

10. The method of claim 9, wherein the brain injury is a traumatic brain injury.

11. The method of claim 9, wherein the brain injury is from a blow to a head of a patient to whom the composition is artificially administered.

12. The method of claim 9, wherein the brain injury is a concussion.

13. The method of claim 9, wherein the brain injury is a non-traumatic brain injury selected from stroke, tumor, hypoxia, infection, and/or encephalitis.

14. The method of claim 9, wherein the composition is a solution having a D-serine concentration of 1 µM to 500 µM.

15. The method of claim 9, wherein artificially administering is achieved by inhalation of the composition.

16. The method of claim 9, wherein artificially administering is achieved by injecting a temporal lobe of the patient's brain with the composition.

17. The method of claim 9, wherein the patient has not been diagnosed with temporal lobe epilepsy when the artificially administering step is performed.

18. A method comprising,
treating a patient having developed a brain injury; and
inhibiting the brain injury from precipitating into temporal lobe epilepsy by artificially administering a composition comprising D-serine to the patient, including an amount of D-serine effective to inhibit death of neurons due to an immune response by glial cells of an injured portion of the patient's brain, wherein artificially administering is achieved by inhalation of the composition.

19. The method of claim 18, wherein the artificially administering step is performed within 170 hours from when the patient received the brain injury.

20. The method of claim 18, wherein the brain injury is a traumatic brain injury.

21. The method of claim 18, wherein the brain injury is from a blow to a head of a patient to whom the composition is artificially administered.

22. The method of claim 18, wherein the brain injury is a concussion.

23. The method of claim 18, wherein the brain injury is a non-traumatic brain injury selected from stroke, tumor, hypoxia, infection, and/or encephalitis.

24. The method of claim 18, wherein the composition is a solution having a D-serine concentration of 1 µM to 500 µM.

25. The method of claim 18, wherein artificially administering is achieved by injecting a temporal lobe of the patient's brain with the composition.

26. The method of claim 18, wherein the patient has not been diagnosed with temporal lobe epilepsy when the artificially administering step is performed.

* * * * *